(12) United States Patent
Chen et al.

(10) Patent No.: US 8,973,572 B2
(45) Date of Patent: Mar. 10, 2015

(54) PRESS-TYPE MEDICAL NEBULIZER AND PRESSING MEANS THEREOF

(75) Inventors: Chun-Hung Chen, New Taipei (TW); Mu-Hua Huang, Taipei (TW)

(73) Assignee: Atlantean Corp., Hsinchu County (TW)

( * ) Notice: Subject to any disclaimer, the term of this patent is extended or adjusted under 35 U.S.C. 154(b) by 779 days.

(21) Appl. No.: 13/267,858

(22) Filed: Oct. 6, 2011

(65) Prior Publication Data
US 2012/0174917 A1 Jul. 12, 2012

(30) Foreign Application Priority Data
Jan. 12, 2011 (TW) .............................. 100200639 U (51) Int. Cl.
*A61M 11/02* (2006.01)
*A61M 11/06* (2006.01)
*A61M 15/00* (2006.01)

(52) U.S. Cl.
CPC ........... *A61M 11/06* (2013.01); *A61M 15/0015* (2013.01); *A61M 15/0018* (2013.01); *A61M 15/002* (2013.01)
USPC ................................ 128/200.23; 128/200.21

(58) Field of Classification Search
USPC ............. 128/200.23, 200.18, 203.12, 203.15, 128/203.23, 205.23, 200.21
See application file for complete search history.

(56) References Cited

U.S. PATENT DOCUMENTS

| 2,829,806 | A | * | 4/1958 | Tedaldi | ..................... 222/402.22 |
| 3,888,422 | A | * | 6/1975 | Robinson | ....................... 239/512 |
| 3,924,768 | A | * | 12/1975 | Lemons | ......................... 215/213 |
| 7,954,487 | B2 | * | 6/2011 | Grychowski et al. | .... 128/200.21 |

FOREIGN PATENT DOCUMENTS

| EP | 170715 A1 * | 2/1986 |
| WO | WO 9944664 A2 * | 9/1999 |

* cited by examiner

*Primary Examiner* — Jackie T Ho
*Assistant Examiner* — Mark Wardas
(74) *Attorney, Agent, or Firm* — Chun-Ming Shih; HDLS IPR Services (57) ABSTRACT

In a press-type medical nebulizer and a pressing means thereof, the nebulizer includes a medicament container having an intake channel and a medical spray generator. The pressing means includes a base, a pressing element and a switching element. The base has a gas-delivering tube, a gas-releasing hole and a trough. The pressing element comprises an operating arm pivotally connected into the trough and a valve for closing the gas-releasing hole. The switching element is slidingly provided on the operating arm to be selectively engaged into the trough for fixing the operating arm. When the switching element is engaged into the trough, the switching element causes the valve to close the gas-releasing hole, so that the pressurized gas can continuously flow through the gas-delivering tube and enter the intake channel. By this arrangement, the user needs not to press the pressing means repeatedly, which is convenient and labor-saving.

16 Claims, 6 Drawing Sheets

PRESS-TYPE MEDICAL NEBULIZER AND PRESSING MEANS THEREOF

BACKGROUND OF THE INVENTION

1. Field of the Invention

The present invention relates to a medicament-feeding device, and in particular to a press-type medical nebulizer and a pressing means thereof.

2. Description of Prior Art

Approximate 70% of human diseases are related to our living environment. The living environment has a great influence on the respiratory system of human beings. In order to treat the diseases of respiratory system, taking oral medicine is the most effective and popular way for patients. However, the oral medicine may be dissolved by the alimentary canal. Thus, the inhalation of liquid medicament is developed, whereby the liquid medicament is delivered to the patient via mouth, nose and lungs. During the inhalation of liquid medicament, a nebulizer is used to produce a medical spray to be inhaled by the patient, so that the medical spray can enter bronchi to spread throughout the pulmonary alveolus. Since the inhalation of liquid medicament has a direct effect on the respiratory tract, the therapeutic effect of the inhalation of liquid medicament is better than that of the oral medicine.

The conventional nebulizer comprises a cylinder, a medical spray generator, a T-shaped pipe in communication with the top of the cylinder, a sleeve and a buffer pipe both in communication with both ends of the T-shaped pipe. A liquid medicament is received in the cylinder, and the medical spray generator is used to atomize the liquid medicament. The free end of the buffer pipe is an open end, so that the patient holds the sleeve in this/her mouth to inhale the medical spray.

When the patient inhales, the medical spray flows from the cylinder through the T-shaped pipe and the sleeve to enter the respiratory tract of the patient. On the other hand, the patient also inhales external air via the buffer pipe to compensate for the necessary quantity of breath. When the patient stops inhaling, the nebulizer still produces the medical spray and the surplus medical spray disperses to the outside via the buffer pipe. Or, when the patient exhales, the exhaled air is exhausted to the outside via the sleeve and the buffer pipe. However, the exhaled air also carries some of the medical spray away from the nebulizer, which causes the waste of medical spray and the contamination of the surrounding environment. Also, it can be understood that the conventional nebulizer has an insufficient efficiency in using the medical spray, so that more medical spray is needed to achieve the desired therapeutic effect, which increases the cost for medical treatment.

The conventional nebulizer is provided with a pressing element. The user presses the pressing element one time to inhale the medical spray generated by the nebulizer. If the user wants to continuously inhale the medical spray in the nebulizer, the user has to press the pressing element for many times, which is inconvenient and laborious for some weak users and patients.

Therefore, it is an important issue for the present Inventor to solve the above-mentioned problems.

SUMMARY OF THE INVENTION

The present invention is to provide a pressing means of a press-type medical nebulizer, which is capable of continuously driving the nebulizer to produce the medical spray based on the demands of a user, and it is convenient and labor-saving in use.

The present invention provides a pressing means of a press-type medical nebulizer, the nebulizer having a medicament container and a medical spray generator disposed in the medicament container, the medicament container having an intake channel, the medical spray generator having a pressurized gas channel, the pressing means including:

a base having a gas-delivering tube and a gas-releasing hole in communication with the gas-delivering tube, the gas-delivering tube being inserted into the pressurized gas channel for allowing the pressured gas to flow through, an outer surface of the base being formed with a trough on the side of the gas-releasing hole;

a pressing element comprising an operating arm pivotally connected into the trough, a valve extending from the operating arm and positioned to correspond to the gas-releasing hole, and an elastic arm connected to the operating arm to abut against the medicament container; and a switching element slidingly provided on the operating arm to be selectively engaged into the trough for fixing the operating arm;

wherein the switching element causes the valve to close the gas-releasing hole when the switching element is engaged into the trough, so that the pressurized gas can continuously flow through the gas-delivering tube and enter the intake channel.

The present invention is to provide a press-type medical nebulizer, which is capable of continuously driving the nebulizer to produce the medical spray based on the demands of a user, and it is convenient and labor-saving in use.

The present invention provides a press-type medical nebulizer, including:

a medicament container having a chamber for storing the medicament and an intake channel;

a medical spray generator disposed in the medicament container and having a pressurized gas channel in communication with the chamber; and a pressing means, comprising:

a base having a gas-delivering tube and a gas-releasing hole in communication with the gas-delivering tube, the gas-delivering tube being inserted into the pressurized gas channel for allowing the pressured gas to flow through, an outer surface of the base being formed with a trough on the side of the gas-releasing hole;

a pressing element comprising an operating arm pivotally connected into the trough, a valve extending from the operating arm and positioned to correspond to the gas-releasing hole, and an elastic arm connected to the operating arm to abut against the medicament container; and a switching element slidingly provided on the operating arm to be selectively engaged into the trough for fixing the operating arm;

wherein the switching element causes the valve to close the gas-releasing hole when the switching element is engaged into the trough, so that the pressurized gas can continuously flow through the gas-delivering tube and enter the intake channel.

In comparison with prior art, the present invention has advantageous features as follows:

The press-type medical nebulizer of the present invention allows the user to produce the medical spray based on his/her demands. When the user presses the pressing means, the medical spray can be produced in the medicament container for inhalation. When the user needs not to inhale the medical spray, the user releases the pressing means to cause the medical spray generator to stop the production of the medical spray. In this way, the medical spray will not be wasted, so that the efficiency in using the medical spray and thus the therapeutic effect are improved.

The present invention has a switching element slidingly provided on the operating arm to be selectively engaged into the trough for fixing the operating arm. When the user pushes the operating arm toward the base to thereby cause the switching element to be engaged into the trough, the valve is caused to close the gas-releasing hole, so that the pressurized gas can continuously flow through the gas-delivering tube and enter the intake channel. In this way, when the user pushes the switching element to be engaged into the trough, the nebulizer can produce the medical spray continuously. Thus, it is not necessary for the user to push the operating arm for many times, which is convenient and labor-saving for the user.

DETAILED DESCRIPTION OF THE INVENTION

The detailed description and technical contents of the present invention will become apparent with the following detailed description accompanied with related drawings. It is noteworthy to point out that the drawings is provided for the illustration purpose only, but not intended for limiting the scope of the present invention.

Please refer to FIGS. 1 to 4. The present invention provides a press-type medical nebulizer and a pressing means thereof. The nebulizer 1 includes a medicament container 100, a medical spray generator 200, and a pressing means 300.

The medicament container 100 comprises a cylinder 110, a shroud 120 and a filter sheet 130.

The cylinder 110 is a hollow cylinder, but its shape is not limited thereto. The size and profile of the cylinder 110 may be designed in other ways as long as the cylinder 110 can be gripped by the user easily. The interior of the cylinder 110 has a chamber 111 penetrating the top of the cylinder 110. The outer surface of the cylinder 110 is provided with a mixed gas exit 112. The periphery of the mixed gas exit 112 protrudes to form an inhalation pipe 113 in communication with the mixed gas exit 112.

The shroud 120 is inserted into an upper space of the chamber 111 to seal the top of the cylinder 110. The shroud 120 comprises a lower cap 121 and a filter casing 122 combined with the lower cap 121.

Figure 4:
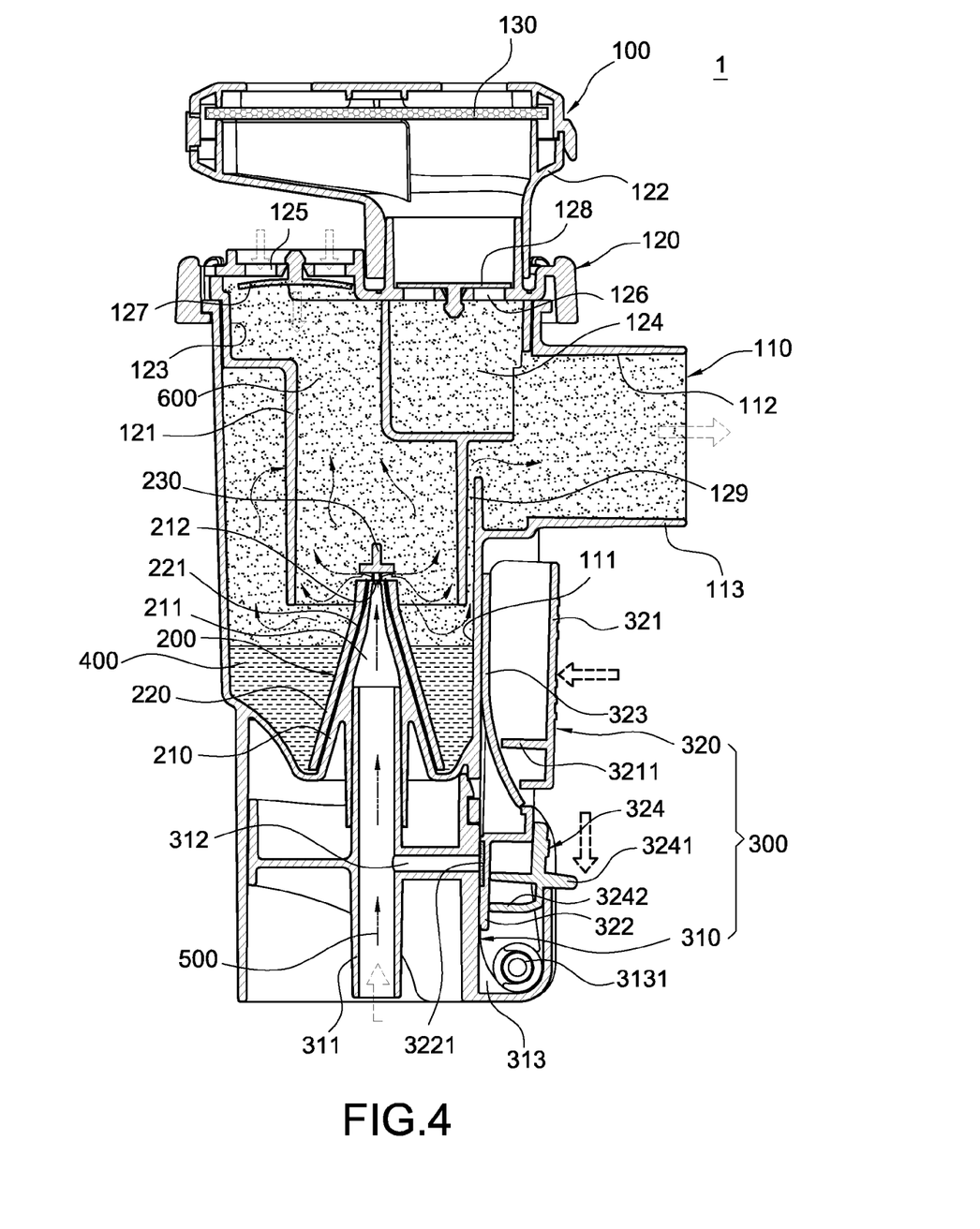
FIG. 4 is a cross-sectional view showing the production of medical spray by the present invention.

The interior of the lower cap 121 are independently formed with an intake channel 123 and an exhaust channel 124. The intake channel 123 is positioned to correspond to the chamber 111, and the exhaust channel 124 is positioned to correspond to the mixed gas exit 112. As shown in FIG. 4, the top surface of the lower cap 121 is provided with an intake hole 125 in communication with the intake channel 123 and an exhaust hole 126 in communication with the exhaust channel 124.

The lower cap 121 has an one-way intake valve 127 disposed across the intake channel 123 for selectively closing the intake hole 125, and an one-way exhaust valve 128 disposed across the exhaust channel 124 for selectively closing the exhaust hole 126. Further, as shown in FIG. 4, a mixed gas channel 129 is formed between the lower cap 121 and the inner wall of the cylinder 110 on the side of the mixed gas exit 112. The mixed gas channel 129 is in communication with the chamber 111 and the mixed gas exit 112.

The filter casing 122 is positioned to correspond to the exhaust hole 126 and connected to the top surface of the lower cap 121. The filter sheet 130 is disposed in the filter casing 122 for filtering the air exhausted from the exhaust hole 126. The filter casing 122 and the filter sheet 130 are optional items because they are used to filter out the virus and bacteria contained in the air exhaled by the patient.

The medical spray generator 200 is inserted inside the lower portion of the cylinder 110. In the present embodiment, the medical spray generator 200 is snap-fitted with the cylinder 110, but the connection there between is not limited to this way only.

The medical spray generator 200 comprises a conical post 210, a conical shroud 220 and a stopping block 230.

Figure 1:
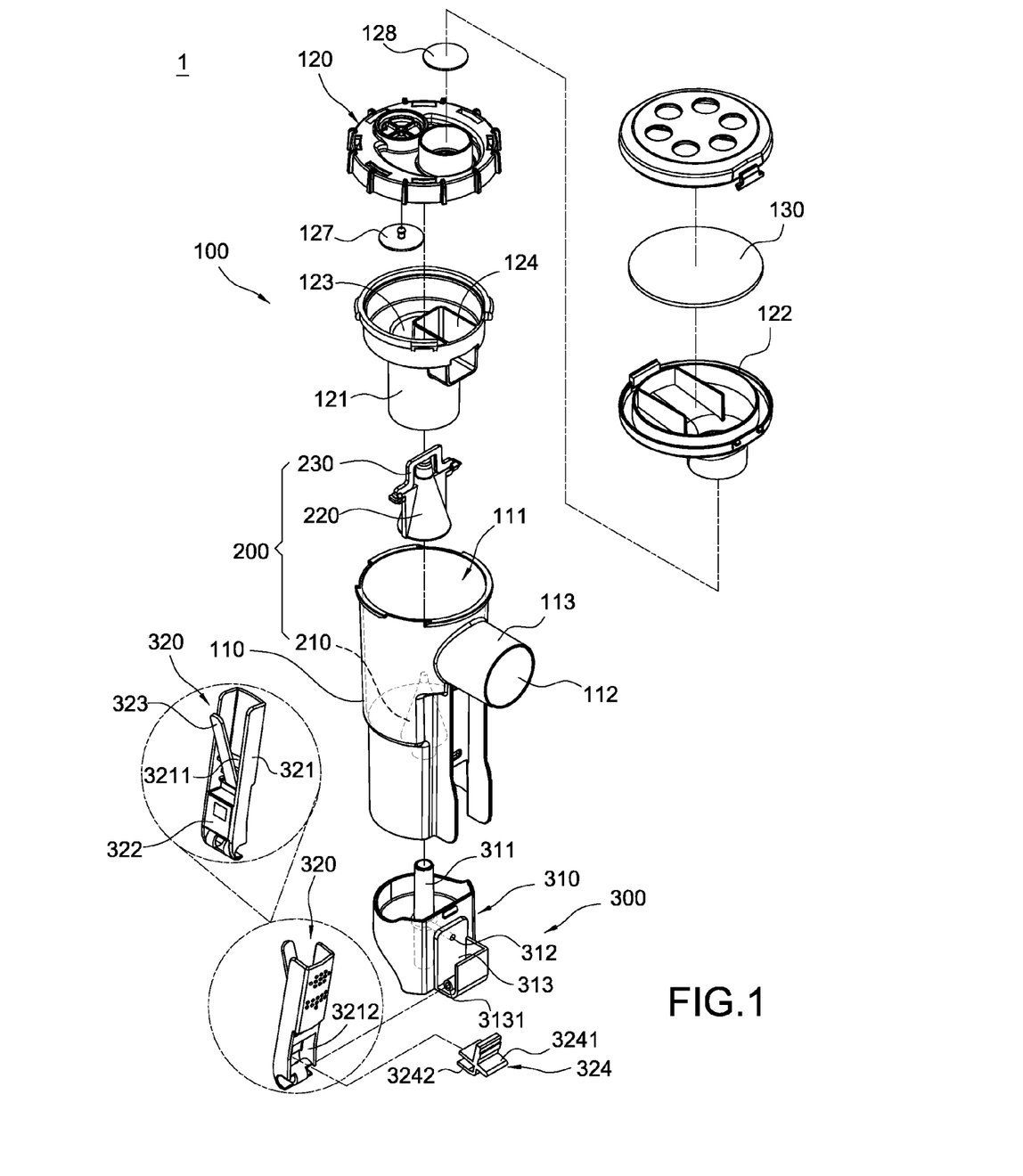
FIG. 1 is an exploded perspective view of the present invention.
Figure 2:
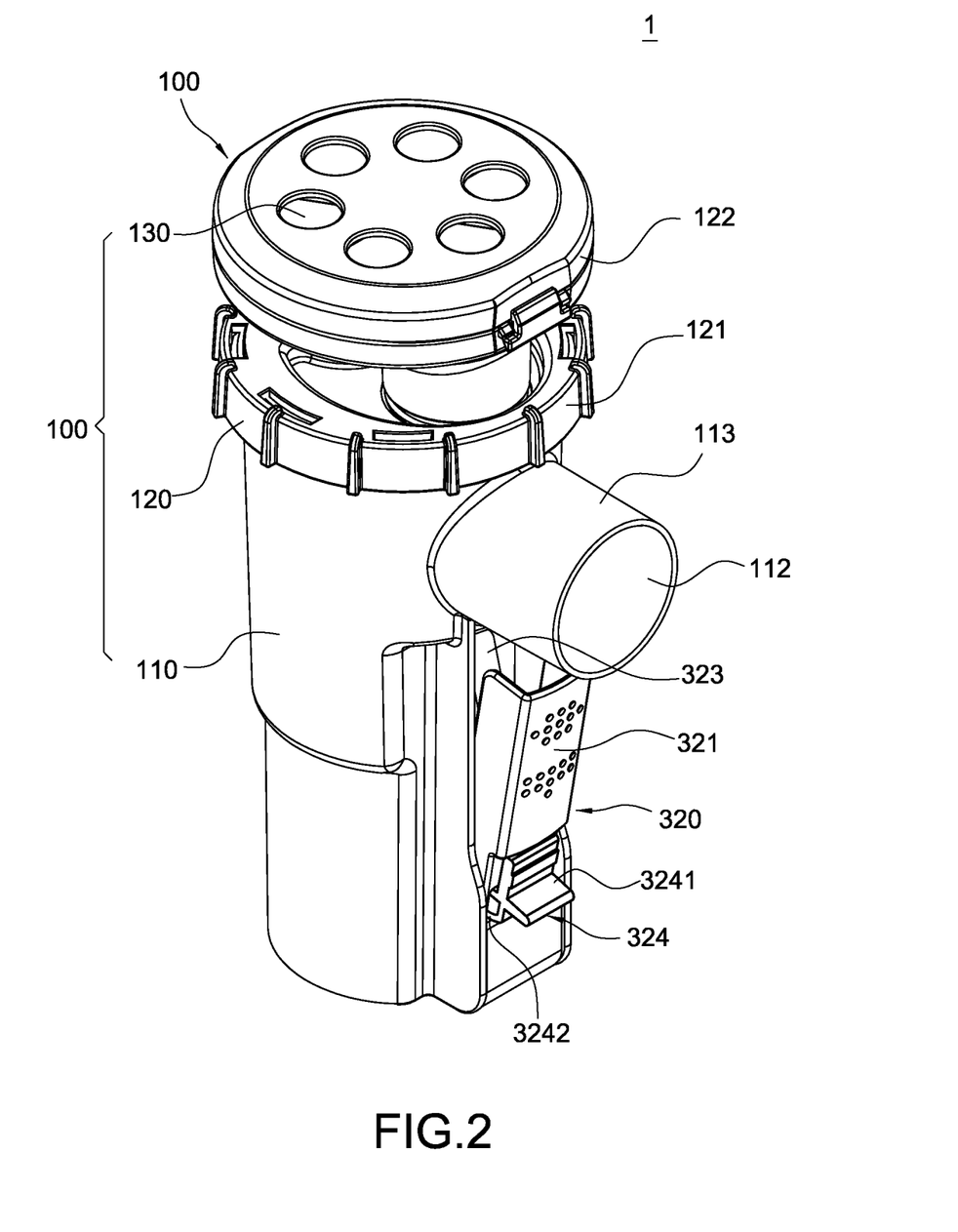
FIG. 2 is an assembled perspective view of the present invention.
Figure 3:
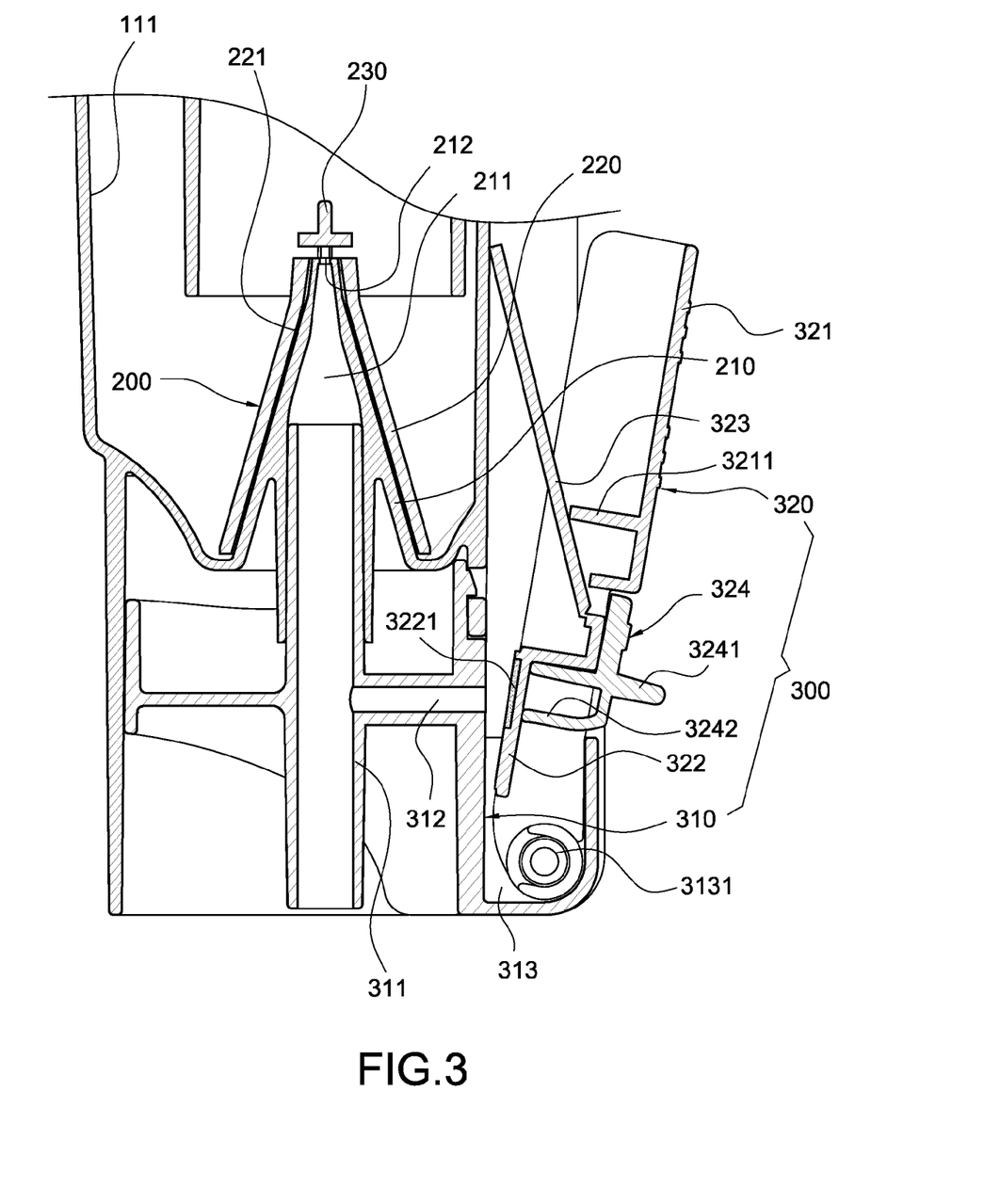
FIG. 3 is a partially assembled cross-sectional view of the present invention.

As shown in FIGS. 3 and 4, the conical post 210 is formed by punching the inner bottom wall of the cylinder 110 toward the chamber 111. The recessed side of the conical post 210 is formed with a pressurized gas channel 211. The top of the conical post 210 is provided with a pressurized gas exit 212 in communication with the chamber 111 and the pressurized gas channel 211.

The conical shroud 220 has a through-hole. The conical shroud 220 is disposed around the protruding side of the conical post 210, so that a gap is formed between the conical shroud 220 and the conical post 210 to form a flow channel 221.

The stopping block 230 is disposed above the conical shroud 220 and the conical post 210 to correspond to the pressurized gas exit 212 and the opening of the flow channel 221.

The pressing means 300 comprises a base 310 and a pressing element 320.

The base 310 comprises a gas-delivering tube 311, a gas-releasing hole 312 and a trough 313. The gas-delivering tube 311 is inserted into the pressurized gas channel 211. The gas-releasing hole 312 is in communication with the gas-delivering tube 311. The central line of the gas-releasing hole 312 is perpendicular to the axial line of the gas-delivering tube 311. The diameter of the gas-releasing hole 312 is larger than that of the pressurized gas exit 212. The trough 313 is formed on the outer surface of the base 310 on the side of the gas-releasing hole 312. The interior of the trough 313 is provided with a pivotal shaft 3131.

The pressing element 320 comprises an operating arm 321, a valve 322, an elastic arm 323, and a switching element 324.

The operating arm 321 is pivotally connected into the trough 313. The valve 322 extends from the operating arm 321 and is positioned to correspond to the gas-releasing hole 312 for selectively closing the gas-releasing hole 312. The elastic arm 323 is connected to the operating arm 321 to abut against the cylinder. The operating arm 321, the valve 322, and the operating arm 323 may be integrally formed into one body, thereby increasing the structural strength, simplifying the production procedure, and reducing the production cost. The elastic arm 323 may be also combined with the operating arm 321 to generate a greater range of elastic deformation. The operating arm 321 is further formed with a press rod 3211 for pressing an outer surface of the elastic arm 323.

The switching element 324 is slidingly provided on the operating arm 321 to be selectively engaged into the trough 313 for fixing the operating arm 321. More specifically, the lower end of the operating arm 321 is formed with a notch 3212. Both inner walls of the notch 3212 are formed with a groove (not shown) respectively. Both sides of the switching element 324 are engaged into the two grooves. The switching element 324 further has a protruding piece 3241 protruding from the notch 3212 and an engaging sheet 3242 selectively engaged into the trough 313.

Figure 5:
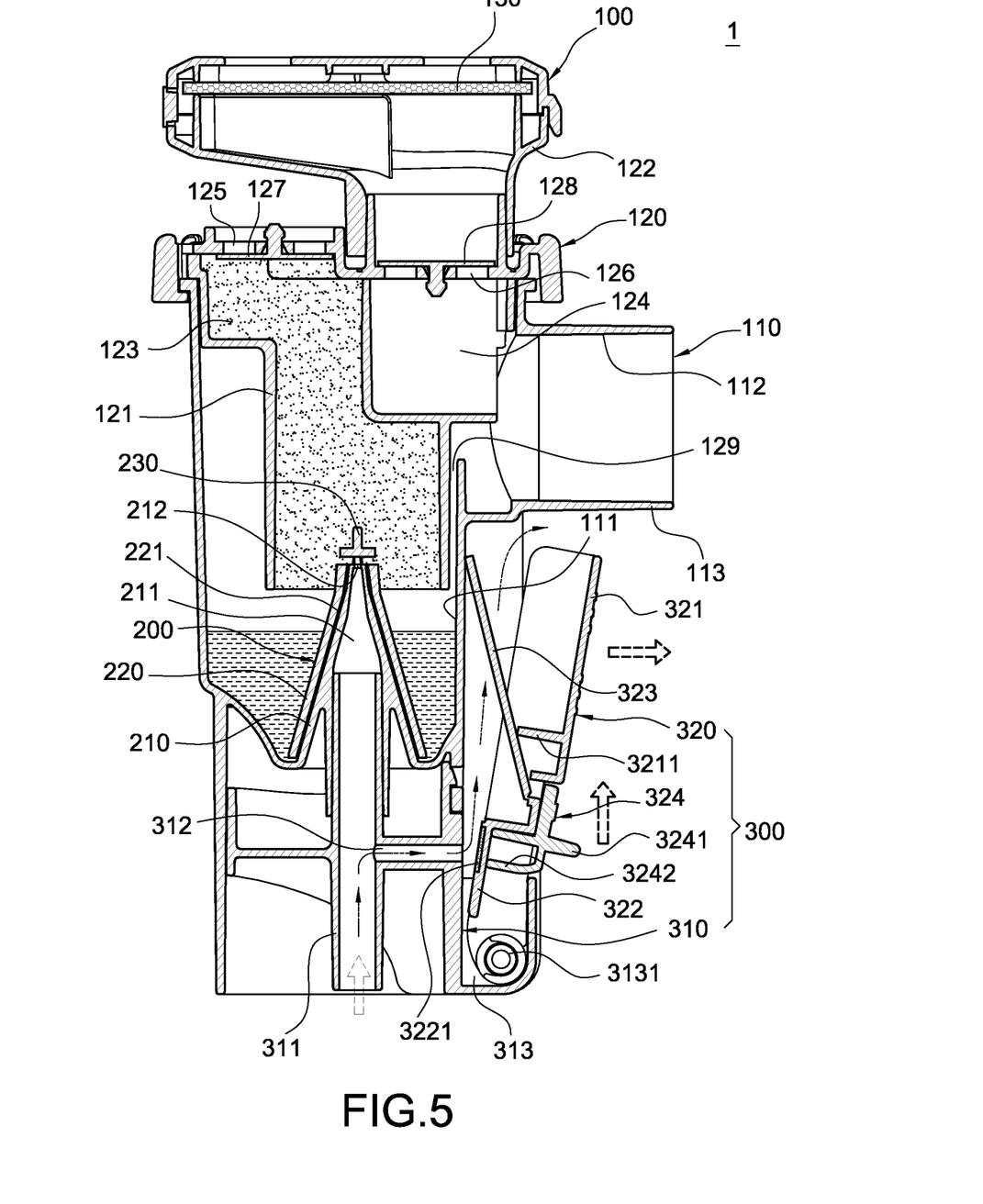
FIG. 5 is a cross-sectional view showing that the production of medical spray by the present invention is stopped.

Please refer to FIGS. 4 and 5. The operating principle of producing the medical spray by the present invention will be described.

First, a medicament 400 is filled in the chamber 111. The medicament 400 is prepared for treating the disease of a patient. The level of the medicament 400 does not exceed the pressurized gas exit 212, and the medicament 400 will flow into the flow channel 221.

Then, a pressurized gas 500 is filled into the gas-delivering tube 311. The pressurized gas 500 usually adopts pressurized oxygen. The pressurized gas 500 flows in the gas-delivery tube 311 and the pressurized gas channel 211.

When the patient needs to inhale the medicament, the patient pushes the operating arm 321 toward the base 310. In this way, the operating arm 321 pivotally rotates around the pivotal shaft 3131 to cause the valve 322 to close the gas-releasing hole 312. At this time, the press rod 3211 presses the elastic arm 323 to generate an elastic deformation.

When the valve 322 closes the gas-releasing hole 312, the only path for the pressurized gas 500 is from the gas-delivering tube 311 to the pressurized gas channel 211. Then, the pressurized gas 500 flows from the pressurized gas channel 211 into the pressurized gas exit 212 of a smaller diameter, which generate a so-called "Venturi Effect". As a result, the pressurized gas 500 draws the medicament 400 out of the flow channel 221.

In order to make the valve 322 to tightly close the gas-releasing hole 312, as shown in FIGS. 3 and 4, a sealing gasket 3221 is disposed on the valve 322 for this purpose. The sealing gasket 3221 is made of soft materials. When the valve 322 abuts against the gas-releasing hole 312, the sealing gasket 3221 prevents the pressurized gas 500 from leaking via the gap between the valve 322 and the gas-releasing hole 312.

The medicament 400 is drawn by the pressurized gas 500, so that the medicament 400 collides with the pressurized gas 500 to become tiny particles. The tiny particles of the medicament 400 is sprayed by the pressurized gas 500 to collide with the stopping block 230, thereby atomizing the medicament 400. The atomized medicament 400 is mixed with the pressurized gas 500 to form a medical spray 600. The thus-formed medical spray 600 is filled in the intake channel 123.

The patient holds the inhalation pipe 113 to inhale the medical spray 600 from the intake channel 123 through the chamber 111, the mixed gas channel 129, the mixed gas exit 112 into his/her lungs. The inhalation of the patient forces the one-way intake valve 127 to open the intake hole 125 and forces the one-way exhaust valve 128 to tightly close the exhaust hole 126.

At this time, the external air enters the intake hole 125 to compensate for the insufficient quantity of breath of the patient. Also, the external air guides most of the medical spray 600 into the mixed gas exit 112, so that the patient can inhale sufficient amount of the medical spray 600 without inhaling too much air. In this way, the efficiency in inhaling the medicament 400 is increased, and the duration of the inhalation treatment is reduced.

If the patient wants to continuously inhale the medical spray 600 without pressing the operating arm 321 repeatedly, as shown in FIG. 4, after the patient pushes the operating arm 321 toward the base 310, he/she can push the protruding piece 3241 of the switching element 324, so that the switching element 324 moves toward the trough 313 until the engaging piece 3242 is engaged in the trough 313. At this time, since the engaging piece 3242 of the switching element 324 is engaged in the trough 313, the operating arm 321 cannot pivotally rotate relative to the trough 313. Thus, the valve 322 continuously closes the gas-releasing hole 312 to make the pressurized gas 500 to continuously flow through the gas-delivering tube 311 and enter the intake channel 123.

As shown in FIG. 5, when the patient wants to stop inhaling the medical spray 600, the patient pushes the switching element 324 back to its original position. Since the engaging piece 3242 is removed from the trough 313, the operating arm 321 can pivotally rotate in the trough 313 by means of the restoring force of the elastic arm 323. In this way, the valve 322 opens the gas-releasing hole 312.

When the gas-releasing hole 312 opens, since the diameter of the gas-releasing hole 312 is much larger than the diameter of the pressurized gas exit 212, the pressurized gas 500 will flow toward a location with smaller resistance by nature. Thus, the pressurized gas 500 disperses to the outside via the gas-releasing hole 312 without entering the pressurized gas exit 212, thereby stopping the production of the medical spray 600.

On the other hand, after the patient inhales the medical spray 600, the patient will subsequently exhale the air in his/her lungs. At this time, the exhalation of the patient forces the one-way exhaust valve 128 to open the exhaust hole 126. The waste air exhaled by the patient is exhausted to the outside via the mixed gas exit 112 and the exhaust channel 124, and then filtered by the filter sheet 130. In this way, the viruses and bacteria contained in the waste air exhaled by the patient can be filtered out without spreading to the outside to contaminate the surrounding environment.

At this time, since the patient is exhaling rather than inhaling, the one-way intake valve 127 closes the exhaust hole 126 again, thereby preventing the medical spray 600 from dispersing to the outside. Further, since the cross-sectional area of the mixed gas channel 129 is much smaller than that of the exhaust channel 124, the waste air exhaled by the patient cannot enter the channel 111 but can be only exhausted to the outside via the exhaust channel 124.

Figure 6:
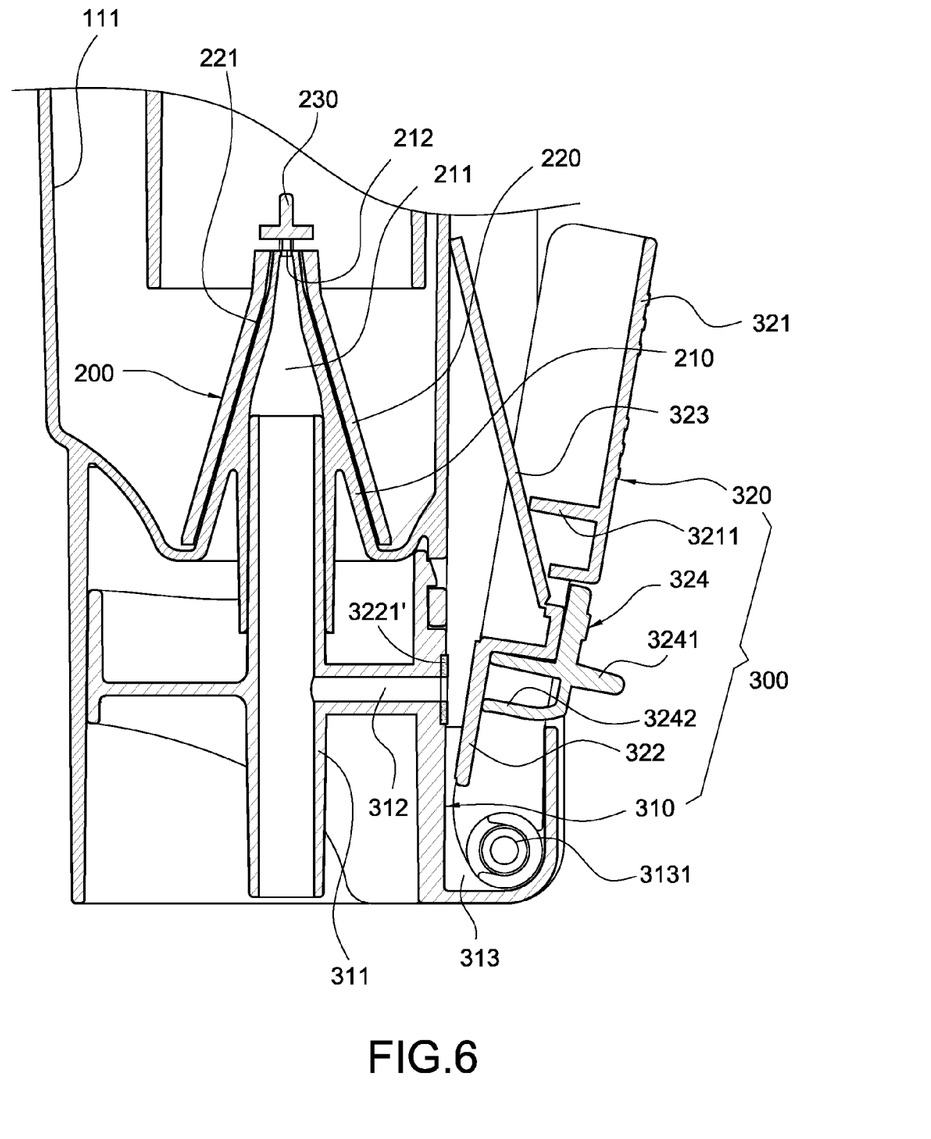
FIG. 6 is a partially assembled cross-sectional view showing another embodiment of the present invention.

Please refer to FIG. 6, which shows another embodiment of the present invention. The difference between the present embodiment and the previous embodiment lies in that: the sealing gasket 3221' is disposed on the periphery of the gas-releasing hole 312 rather than on the valve 322. The sealing gasket 3221' is also made of soft materials. When the valve 322 abuts against the gas-releasing hole 312, the sealing gasket 3221' can prevent the pressurized gas 500 from leaking to the outside via the gap between the valve 322 and the gas-releasing hole 312.

The present invention indeed demonstrates convenience. The patient only needs to press the pressing means 300 to inhale the medical spray 600. When the patient releases the pressing means 300, the production of the medical spray 600 is stopped. Thus, the waste of the medicament 400 and the medical spray 600 is reduced. Also, the efficiency in using the medicament and the therapeutic effect are increased. On the other hand, during the inhalation treatment, the exhalation of the patient does not force the medical spray 600 to exhaust from the chamber 111, so that the medicament 400 and the medical spray 600 can be saved. Further, the waste air exhaled by the patient can be filtered by the filter sheet 130, thereby preventing the virus and bacteria contained in the waste air from spreading to the outside to contaminate the surrounding environment.

Moreover, the user can push the switching element 324 to be engaged in the trough 313 based on his/her demands, so that the nebulizer 1 of the present invention can produce the medical spray 600 continuously. Thus, the user needs not to press the operating arm 321 repeatedly, which is convenient and labor-saving for the user.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. A pressing means of a press-type medical nebulizer, the nebulizer having a medicament container and a medical spray generator disposed in the medicament container, the medicament container having an intake channel, the medical spray generator having a pressurized gas channel, the pressing means including:
   a base having a gas-delivering tube and a gas-releasing hole in communication with the gas-delivering tube, the gas-delivering tube being inserted into the pressurized gas channel for allowing the pressured gas to flow through the pressurized gas channel, a wall protruding from an outer surface of the base and further bent upward to form a trough on the side of the gas-releasing hole;
   a pressing element comprising an operating arm pivotally connected into the trough, a valve extending from the operating arm and positioned to correspond to the gas-releasing hole, and an elastic arm connected to the operating arm to abut against the medicament container; and
   a switching element being directly against the valve and slidingly provided on the operating arm to be selectively engaged into the trough for fixing the operating arm;
   wherein when the operating arm is in a released position, the elastic arm is relaxed and keeps the operating arm away from the base, and the wall restricts the switching element from sliding into the trough; when the operating arm is in a pressed position, the elastic arm deforms by pushing the operating arm, and the switching element is slidably engaged into the trough;
   wherein the switching element is allowed to slide into the trough to be directly clamped between the valve and the wall to prevent the operating arm back to the released position due to the elastic force of the elastic arm;
   wherein the switching element keeps the valve closing the gas-releasing hole when the switching element is engaged into the trough in the pressed position, so that the operating arm is fixed to the pressed position and the pressurized gas can continuously flow through the gas-delivering tube and enter the intake channel.

2. The pressing means of a press-type medical nebulizer according to claim 1, wherein the operating arm is formed with a press rod for pressing an outer surface of the elastic arm and a notch in which the switching element is slidingly disposed.

3. The pressing means of a press-type medical nebulizer according to claim 2, wherein the switching element has a protruding piece protruding from the notch and an engaging piece selectively engaged in the trough.

4. The pressing means of a press-type medical nebulizer according to claim 3, wherein the valve is provided with a sealing gasket, and the sealing gasket is made of soft materials for sealing a gap between the valve and the gas-releasing hole.

5. The pressing means of a press-type medical nebulizer according to claim 3, wherein the periphery of the gas-releasing hole is provided with a sealing gasket, and the sealing gasket is made of soft materials for sealing a gap between the valve and the gas-releasing hole.

6. A press-type medical nebulizer, including:
   a medicament container having a chamber for storing a medicament and an intake channel;
   a medical spray generator disposed in the medicament container and having a pressurized gas channel in communication with the chamber; and
   a pressing means, comprising:
   a base having a gas-delivering tube and a gas-releasing hole in communication with the gas-delivering tube, the gas-delivering tube being inserted into the pressurized gas channel for allowing the pressured gas to flow through the pressurized gas channel, a wall protruding from an outer surface of the base and further bent upward to form a trough on the side of the gas-releasing hole;
   a pressing element comprising an operating arm pivotally connected into the trough, a valve extending from the operating arm and positioned to correspond to the gas-releasing hole, and an elastic arm connected to the operating arm to abut against the medicament container; and
   a switching element being directly against the valve and slidingly provided on the operating arm to be selectively engaged into the trough for fixing the operating arm;
   wherein when the operating arm is in a released position, the elastic arm is relaxed and keeps the operating arm away from the base, and the wall restricts the switching element from sliding into the trough; when the operating arm is in a pressed position, the elastic arm deforms by pushing the operating arm, and the switching element is slidably engaged into the trough;
   wherein the switching element is allowed to slide into the trough to be directly clamped between the valve and the wall to prevent the operating arm back to the released position due to the elastic force of the elastic arm;
   wherein the switching element keeps the valve closing the gas-releasing hole when the switching element is engaged into the trough in the pressed position, so that the pressurized gas can continuously flow through the gas-delivering tube and enter the intake channel.

7. The press-type medical nebulizer according to claim 6, wherein the medicament container comprises a cylinder having the chamber, and a shroud connected to one end of the cylinder, the cylinder is provided with a mixed gas exit in communication with the chamber, the intake channel is positioned to correspond to the chamber, and the shroud has an exhaust channel positioned to correspond to the mixed gas exit.

8. The press-type medical nebulizer according to claim 7, wherein the shroud comprises a lower cap, the intake channel and the exhaust channel are independently formed in the lower cap, and a mixed gas channel is formed between the lower cap and the cylinder in communication with the chamber and the mixed gas exit.

9. The press-type medical nebulizer according to claim 8, wherein the lower cap is provided with an intake hole in communication with the intake channel, and an exhaust hole in communication with the exhaust channel, the lower cap comprises an one-way intake valve positioned across the intake channel for selectively closing the intake hole, and an one-way exhaust valve positioned across the exhaust channel for selectively closing the exhaust hole.

10. The press-type medical nebulizer according to claim 9, wherein the medicament container further comprises a filter sheet positioned to correspond to the exhaust hole for filtering the air exhausted from the exhaust hole, the shroud further comprises a filter casing positioned to correspond to the exhaust hole and connected to the lower cap, and the filter sheet is disposed in the filter casing.

11. The press-type medical nebulizer according to claim 10, wherein the medical spray generator comprises a conical post formed in the cylinder and a conical shroud disposed around the conical post, the pressurized gas channel is formed on a recessed side of the conical post, the conical post is provided with a pressurized gas exit in communication with the chamber and the pressurized gas channel, and a flow channel is formed between the conical shroud and the conical post.

12. The press-type medical nebulizer according to claim 11, wherein the medical spray generator further comprises a stopping block positioned to correspond to the pressurized gas exit and the flow channel.

13. The press-type medical nebulizer according to claim 12, wherein the operating arm is formed with a press rod for pressing an outer surface of the elastic arm and a notch in which the switching element is slidingly disposed.

14. The press-type medical nebulizer according to claim 13, wherein the switching element has a protruding piece protruding from the notch and an engaging piece selectively engaged in the trough.

15. The press-type medical nebulizer according to claim 14, wherein the valve is provided with a sealing gasket, the sealing gasket is made of soft materials for sealing a gap between the valve and the gas-releasing hole.

16. The press-type medical nebulizer according to claim 14, wherein the periphery of the gas-releasing hole is provided with a sealing gasket, and the sealing gasket is made of soft materials for sealing a gap between the valve and the gas-releasing hole.

* * * * *